US006248782B1

(12) United States Patent
Elford et al.

(10) Patent No.: US 6,248,782 B1
(45) Date of Patent: Jun. 19, 2001

(54) METHOD OF TREATING VIRAL DISEASES

(76) Inventors: Howard L. Elford, 3313 Gloucester Rd., Richmond, VA (US) 23227; Bartholomeus van't Riet, 3419 Noble Ave., Richmond, VA (US) 23222

( * ) Notice: Subject to any disclaimer, the term of this patent is extended or adjusted under 35 U.S.C. 154(b) by 0 days.

(21) Appl. No.: 08/183,181

(22) Filed: Jan. 18, 1994

Related U.S. Application Data

(63) Continuation-in-part of application No. 07/785,982, filed on Oct. 31, 1991, now abandoned.

(51) Int. Cl.[7] ............... A61K 31/265; A61K 31/205; A61K 31/185
(52) U.S. Cl. .............. 514/512; 514/554; 514/555; 514/576
(58) Field of Search .................... 514/512, 554, 514/555, 576

(56) References Cited

U.S. PATENT DOCUMENTS

| 1,715,251 | 5/1929 | Sabalitschka . | |
|---|---|---|---|
| 2,952,583 | 8/1960 | Fritts . | |
| 4,623,659 | 11/1986 | van't Riet et al. | 514/508 |
| 4,946,868 | 8/1990 | Demarne et al. | 514/544 |
| 5,521,161 | 5/1996 | Malley et al. | 514/45 |
| 5,736,526 | 4/1998 | Malley et al | 564/301 |
| 5,736,527 | 4/1998 | Malley et al. | 514/45 |

FOREIGN PATENT DOCUMENTS

| 227100 | 7/1987 | (EP) . | |
|---|---|---|---|
| 393031 | 11/1979 | (SU) . | |
| WO84/04676 | * 6/1984 | (WO) | A61K/31/15 |
| WO 94/27590 | 5/1993 | (WO) . | |

OTHER PUBLICATIONS

Sharma, Lien et al Progess in Drug Research in Drug Research 31 101 (1(87)) 1987.
Biron et al J. Aquired Immune Deficiency Syndrome & Human Retrovirology 10 36 (1995).
35th ICAAC Abstracts Williams et al, 1995.
HIV–Issues In Patient Carevol. 2 pp. 1 and 14 (1999).
Antiviral Agents Bulletin vol. 12 No. 5 pp. 134–135 (1999).
Gelone et al 56 Am. J. Health–Sys Pharm, 1554 (1999).
Law et al J.N.C.I.pp. 179–192 (1940).
Skipper et al Cancer Res. pp. 717–726 (1957).
Moore et al J.N.C.I. 36 405 (1966).
Himmelfarb et al Cancer Chemo. Repts. 7 451 (1967).
Bonmasser et al Cancer Res. 32 1446 (1972).
Chen et al ibid 35 718 (1975).
Allaudeen & Bertino J.N.C.I. 59 227 (1977).
Kennel et al. Cancer Res. 38 4574 (1978).
Marcus et al Biochem & Biophys. Res Comm. 142 422 (1987).
HIV Suppressionetc, Lancet 352 199 (1998).
Use of Didox & Trimidox with ddl in Aids Treatment Cell & Mol. Biol. 43 1019 (1997) Mayhew et al.
Abstract 5th Int. Conf. on Antiviral Res. Mar. 8–13, 1992 Mills, Elford, van't Riet and Webb.
Abs. Am. Assoc. can. Res. 1992 DIDOX Exhibits Activity in a Retrovirus Animal Model Mills et al.
Gao et al Nat Acad. Sci. 90 8925 (1993).
Roederer et al Nat. Acad. Sci. 87 4844 (1992).
Schreck et al *J. Virol.* 6228 (1992).
AIDS Treatment News No. 178 Jul. 9, 1993.
Atta et al *Biochem J* 290 807 (1993).
Kjoellor et al Chem. Abs 97 1061845 (1982).
Ruprecht et al *Can. Res*(Suppl) 50 6158 (1990).
Johnson et al *Can. Res*(Suppl) 50 5682a (1990).
Reichard *J.B.C.* 268 8383 (1993).
Staal et al, AIDS Research and Human Retroviruses, vol. 9, p. 299, 1993.
Summers et al, Cell vol. 29. pp. 403–415, 1992.*
Tiollais et al, Scientific American, Apr., pp. 116–123, 1991.*
T'et al, J Med chem, vol. 28, 1103–06, 1985.*
Yeh et al 1978, 88 CA:1325668t.*
Najean et al 79 CA:13527h 1973.*
Honda et al 1991 115 CA:197735R.*
Gale et al, 1968, Experieutia, vol. 24 (2) p 194–95.*
Douvas et al, 1991 (Jul.), P.N.A.S. vol. 88 pp 6328–6332.*

* cited by examiner

Primary Examiner—William R. A. Jarvis

(57) ABSTRACT

A therapeutic process for treating disease in mammals caused by retroviruses in which the infected mammal is treated with a ribonucleotide reductase inhibitor such as a polyhydroxy benzoic, mandelic or phenylacetic acid derivative, such as N,3,4-trihydroxybenzamide, a hlydroxyurea, a thiosemicarbazone or other ribonucleotide reductase inhibitor. The polyhydroxybenzoic acid derivatives are also useful in the treatment of diseases in mammals caused by DNA viruses.

19 Claims, No Drawings

METHOD OF TREATING VIRAL DISEASES

CROSS-REFERENCE

This application is a continuation-in-part of application Ser. No. 07/785,982, filed Oct. 31, 1991, now abandoned.

BACKGROUND OF THE INVENTION

This invention relates to a method of treating diseases in mammals caused by retroviruses. This invention also provides methods for treating diseases in mammals caused by a DNA virus. The term "DNA virus" is defined as being a virus with a DNA genome and the term "retrovirus" is defined as being a RNA virus having a reverse transcriptase (RNA-dependent DNA polymerase) within the virion, according to the TEXTBOOK OF HUMAN VIROLOGY, 2nd ed. R. B. Belshe Ed., (Mosby, St. Louis 1991). Replication of the viral RNA involves a DNA provirus that is integrated into host cellular DNA. Among mammalian diseases caused by DNA viruses which can be treated by the therapeutic processes of this invention are included the Paroviruses which can infect both rodents (Kilham's virus, Aleutian mink disease) and humans (Parovirus strain B19 and RA-1 virus), the Papovaviruses which include the Papilloma viruses which can infect rabbits (Shope papillomavirus), and the Polyomaviruses which infect primates (vacuolating virus of Rhesus monkeys and JC and BK viruses of man). JC virus is associated with progressive multifocal leukoencephalopathy (PML). Other diseases caused by DNA viruses which can be treated by the processes of this invention are those caused by the Adenoviruses which cause acute respiratory diseases, febrile catarrhs, pharyngitis and conjunctivitis of man, the Herpes viruses which cause both latent and persistent infection in man including Epstein-Barr herpes virus (Lymphocryptovirus) associated with human Burkitt's lymphoma, nasopharyngeal carcinoma and causes infectious mononucleosis in man; *Herpes simplex* which causes both fever blisters and genital herpes among other human diseases, Simian B virus, often fatal to man; *Herpes zoster* (Varicellovirus) which causes infectious mononucleosis and shingles in man; Betaherpes viruses which are associated with cytomegalic inclusion disease and infection of T and B cell leukocytes; the Hepadnaviruses which, upon infection in man are associated with hepatitis, hepatocellular carcinoma and immune complex-mediated extrahepatic injury including hepatitis B and three similar viruses are found in wood ducks, ground squirrels and domestic ducks.

Retroviral diseases in mammals which are treatable by the therapeutic processes of this invention include those caused by the RNA tumor viruses (oncoviruses) and the slow viruses (lentiviruses). Specific oncovirus caused diseases include, in man, T-cell leukemia induced by human T-cell lymphotropic viruses (HTLV-I and II). In addition, there are oncovirus caused diseases other than human which include sarcoma and leukemic diseases of cats, birds, hamsters and primates. Among the lentiviruses caused diseases, HIV which causes AIDS in man is the most prominent. Lentiviruses which cause diseases in mice include murine C-type retroviruses which cause leukemias, such as Friend leukemia, Rauscher, Abelson, Gross and Moloney viruses. Murine lentiviruses causing sarcomas include Kirsten, Harvey, Moloney, Balb and FBJ.

Ideally, virus suppression in an infected mammal by one or more drugs would be the treatment of choice; that is to say, to find a drug which can kill the infecting virus on contact. However, no such drug is currently available, and a more attainable goal would involve discovering a drug which can prevent viral reproduction. One of the major problems in developing such a treatment method for persons infected with one or more DNA or retroviruses is the occurrence of an asymptomatic viremia in mammals lasting from several weeks to several years or, in the case of *Herpes simplex* infections, of recurrent episodes after periods of dormancy while the human subject still harbors the virus. Thus, a useful method of treating a retroviral disease would be to use a drug that can destroy all cells harboring latent virus, rather than simply finding a drug which is only useful after an initial exposure and acts by preventing implanting of the virus or provirus into host chromosomal cells or by inhibiting other early steps in the viral replication cycle. Another therapeutic approach would be to find a drug capable, in the case of HIV-I or II infections, of stimulating the immune system of the host. AZT, the first drug currently approved for the treatment of AIDS, is targeted against reverse transcriptase, an enzyme with a critical function in the early part of the retroviral life cycle. Unfortunately, AZT can cause anemia after prolonged administration.

A second major problem which has hindered the search for effective anti-AIDS drugs has been the lack of an animal model. Ruprecht et al CANCER RESEARCH (SUPPL.) 50 5618a Sept. 1, 1990 describe and evaluate the various models then available for evaluating antiretroviral therapy. Johnson et al ibid 5682 have described a useful murine model which utilizes the retrovirus, Friend leukemia virus, in what is described as a Friend Virus-induced ErythroLeukemia Model. This system for the first time enables investigators to evaluate various anti-retroviral treatment methods and drugs useful in such methods as candidates for the therapy of AIDS and other retroviral diseases.

To date, there has been no publication demonstrating a relationship between ribonucleotide reductase inhibitors and antiretroviral activity, particularly against HIV except for a recent publication Gao et al, Proc. Natl. Acad. Sci. USA, 90:8925–8928 (1993).

SUMMARY OF THE INVENTION

This invention provides a therapeutic process for the treatment of diseases caused by retroviruses in mammals which therapeutic process comprises administering to a mammal suffering from one or more of said viral diseases and in need of treatment, an effective amount of a ribonucleotide reductase inhibitor sufficient to-treat said viral disease in said mammal. Among the ribonucleotide reductase inhibitors which are useful in the therapeutic processes of this invention, we particularly prefer derivatives of polyhydroxy-substituted benzamides and phenylacetamides derivatives of the following formula:

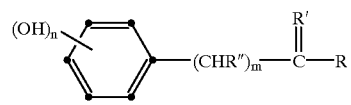

Formula I wherein n is 2–5, m is 0 or 1, R is $NH_2$, NHOH, $OC_{1-3}$ alkyl or O-phenyl, R' is O, NH or NOH and R" is H or OH. Also included are the pharmaceutically-acceptable salts of compounds according to the above formula where chemically feasible. Also included within the scope of this invention are the phenolic acetyl derivatives of compounds according to the above formula. Such acetyl derivatives act as "prodrugs" in that they are converted by the mammalian body to the corresponding compound having entirely unesterified phenolic hydroxyls, which are the therapeutically active drugs.

Illustrative of the polyhydroxy-substituted phenyl ring in the above formula are included 2,3-dihydroxyphenyl, 3,4-dihydroxyphenyl, 2,5-dihydroxyphenyl, 2,6-dihydroxyphenyl, 2,3,4-trihydroxyphenyl, 2,3,5-trihydroxyphenyl, 3,4,5-trihydroxyphenyl, 2,4,5-trihydroxyphenyl, 2,3,4,5-tetrahydroxyphenyl, pentahydroxyphenyl and the like groups.

In the above formula, when m is 1 and R" is H, a phenylacetic acid derivative is denominated. When m is 1 and R" is OH, a mandelic acid derivative is represented. When m is O, R is NHOH and R' is O, an N-hydroxybenzamide (formerly, a benzohydroxamic acid) is represented; when R is $NH_2$ and R' is NH, a benzimidamide (formerly a benzamidine) is represented; when R is NHOH and R' is NH, an N-hydroxy benzimidamide (formerly a benzamidoxime) is shown; when R is NHOH and R' is NOH, an N,N'-dihydroxy benzimidamicle (formerly, an hydroxyamidoxime) is represented; and when R is O-alkyl or O-phenyl and R' is NH, the resulting compounds are benzimidates (rather than benzamidates as previously). In the above formula, when R is $OC_{1-3}$ alkyl, the alkyl groups represented include methyl, ethyl, isopropyl and n-propyl.

Compounds represented by the above formula are fully illustrated in U.S. Pat. Nos. 4,253,322, 4,623,659, 2,848,430 and 3,629,443. Methods for their preparation are also fully disclosed in those patents as well as in the many references cited therein. In particular, the compounds listed in Cols. 2 and 3 of U.S. Pat. No. 4,623,659 illustrate the scope of the compounds represented by the above formula (always remembering that the approved nomenclature for these structures has changed since 1983 when the application which resulted in that patent was filed) and the disclosure of U.S. Pat. No. 4,623,659 is incorporated herein, and made a part of, by reference.

There is a further group of miscellaneous polyhydroxy phenyl ribonucleotide reductase inhibitors useful in the therapeutic processes of this invention which can be represented by the following formula

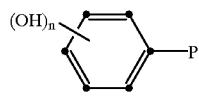

Formula II wherein, as before, n is 2–5 and P can be COOH, CN, $C_1$–$C_8$ alkyl, aryl-substituted $C_1$–$C_8$ alkyl, acylamino, $HOC_2H_4$—NH—$CH_2$—C(=O)—, C1—$C_2H_4$—$NCH_3$—$CH_2$—C(=O)—, C(=S)$OC_2H_5$, C(=O)—NH—$C_{1-3}$ alkyl, C(=NH)—N(OH)—$C_{1-3}$ alkyl and substituted variants thereof.

It will be apparent that other phenolic blocking groups, such as the acetyl group specified earlier, may be employed to yield pro-drugs which groups in the mammalian body are removed to yield drugs containing only free phenolic hydroxyls. Such alternative blocking groups include esters of other alkanoic acids, phenacyl esters and the like.

A third group of ribonucleotide reductase inhibitors that we find particularly useful in the therapeutic processes of this invention are hydroxyurlea derivatives of the following formula $R^3Z$, wherein $R^3$ is H, $NH_2$, $NH_2$—NH, NHOH, NOH—$R^6$, $C_1$–$C_6$ alkyl, $OC_{1-6}$ alkyl, aryl-substituted $C_1$–$C_6$ alkyl, phenyl, naphthyl, pyridyl, pyrimidyl or thienyl and wherein Z is C(=O)NOH—$R^4$, C(=S)—NOH—$R^4$, C(=NH)—NOH—$R^4$, C(=NOH)—$C_1$-$C_3$ alkyl, C(=NOH)—$R^4$ and C(=NOH)—$R^5$, wherein $R^4$ is H, $C_1$–$C_6$ alkyl and substituted $C_1$–$C_6$ alkyl, wherein said substituents can be hydroxy, alkoxy, amino or halo, and wherein $R^5$ is $NH_2$ or NHOH, wherein $R^6$ is $C_{1-6}$ acyl, alkyl and substituted $C_{1-6}$ alkyl, wherein said substitutes can be hydroxyl, alkoxy, amino or halo and the like. The above group of compounds are generally referred to as "hydroxyureas." A publication outlining the structure-activity relationships as inhibitors of the biosynthesis of deoxyribonucleotides of a group of hydroxyurea derivatives was published by Young, et al., *CANCER RES.* 27 (Part 1) 635 (1967). Hydroxyurea itself is currently marketed as an anti-neoplastic agent.

A fourth group of ribonucleotide reductase inhibitors useful in the therapeutic process of this invention include the semithiocarbazones of 2-formylpyridine, 2-acetylpyridine, 1-formylisoquinoline, 1-acetylisoquinoline, and of their ring substituted analogs. Formulas 4 and 5 below illustrate their composition

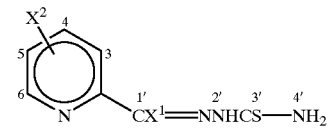

Formula 4

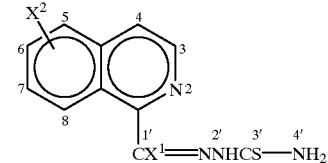

Formula 5 wherein Formula 4 represents pyridine and Formula 5, isoquinoline-semithiocarbazones, in which $X^1$ is H or $CH_3$, $X^2$ is H, OH, $NH_2$, F, $CF_3$, $C_{1-3}$ alkyl, $OX^3$, $NHX^3N(X^3)_2$, and O(O=C)$X^4$, in which $X^3$ denotes $C_{1-3}$ alkyl and $X^4$ is aryl, $C_{1-6}$ alkyl including substitutions on the alkyl chain of the carboxylic acid with $C_{1-3}$ alkoxy, $C_{1-3}$ mono- or di-alkylamino, aryloxy, also those in which the aryl ring is substituted with one or more hydroxy, amino or ch-Loro groups. Also included are the pharmaceutically acceptable salts of compounds according to the above formulas where chemically feasible. Both E and Z isomers of the compounds and their mixtures are included in this invention.

Illustrate of the 2-formylpyridine and 2-acetylpyridine thiosemicarbazone derivatives useful in the therapeutic process of this invention are included 3-hydroxy, 3-amino, 3-methyl, 3-methoxy, 3-acetoxy, 3-ethoxy, 3-fluoro, 5-hydroxy, 5-amino, 5-fluoro, 5-trifluoromethyl, 5-methoxy, 5-ethoxy, 5-dimethylamino, 5-pivaloyloxy, 5-phenoxyacetoxy, 5-N, N-dimethylaminoacetoxy, and 3,4-dihydroxybenzoyloxy as ring substituents. Illustrative of the 1-formylisoquinoline and 1-acetylisoquinoline thiosemicarbazone derivatives useful in the therapeutic process of this invention are included 4-hydroxy, 4-methyl, 4-amino, 5-fluoro, 5-trifluoromethyl, 5-amino and 5-acetylamino as ring substituents. A publication outlining the structure-activity relationship as inhibitors of ribonucleotide reductase and in vivo antitumor activity of 2-formylpyridine and 1-formylisoquinoline thiosemicarbazone derivatives was published by French et al, J. Med. Chem. 17:172 (1974).

It will be apparent to those skilled in the art that other ribonucleotide reductase inhibitors in addition to those enumerated above would also be operative in the processes of this invention and are therefore included within its scope.

In a second aspect of this invention are therapeutic processes for the treatment of diseases in mammals utilizing as the treatment drug, an effective amount of a compound according to Formula I above. Of particular interest is the treatment of DNA viral diseases in mammals, caused by Herpes viruses, particularly Herpes simplex and Herpes zoster (varicellovirus); Hepatitis B and other Hepadna viruses.

As previously stated, the therapeutic processes disclosed by this invention are useful in suppressing the growth or reproduction of DNA viruses and retroviruses in mammals, including primates such as new-world monkeys, and the great apes including man, in rodents, ungulates (both cattle and sheep), in horses, swine, mink, etc. Illustrations of such therapeutic processes, utilizing the retrovirus Friend leukemia virus in mice, are given in the Biological Testing Section.

BIOLOGICAL TESTING

To test the ability of the compounds of the above formula to suppress the growth of retroviruses in vivo, the following protocol was used: six week old female mice (B6D2/F1 hybrids) were infected with Friend leukemia virus (FLV) on day 0. The FLV employed is classified as a murine leukosis sarcoma complex retrovirus that causes red blood cell tumors in the spleen resulting in splenomegaly and was obtained from the American Type Culture Collection, ATCC No. VR-245. The drug was administered parenterally (via the intraperitoneal route) daily for 12 days starting on day 1. The mice were sacrificed on day 14 for collection of spleen, liver and blood. In an initial experiment, the treatment groups included the following: Didox (N,3,4-trihydroxybenzamide) at 450 mg/kg, Amidox (N,3,4-trihydroxybenzimidamide as the HCl salt) at 225 mg/kg, FLV-infected saline control, saline control. There were four mice per treatment group. Table 1 below gives the spleen and liver weights for the four groups.

TABLE 1

Relative Spleen and Liver Weights, Didox and Amidox

| TREATMENT GROUP | SPLEEN WT.** | LIVER WT.** |
|---|---|---|
| | Mean ± S.E. | |
| Saline Control | 0.33 ± 0.1* | 4.76 ± .11 |
| FLV-Saline | 6.20 ± 1.73 | 5.62 ± .40 |
| FLV-Didox | 0.47 ± .06* | 4.88 ± .26 |
| FLV-Amidox | 1.48 ± .48 | 4.76 ± .11 |

* = statistically significant at alpha = 0.05
** = % of body weight
FLV = Friend leukemia virus infected group of mice.

Blood cell count data on the above groups plus a Didox and an Amidox uninfected group (at the same dose rate as with the infected groups) as a further control gave the results given in Table 2 below.

TABLE 2

Blood Count and Percent Reticulocytes for Table 1 Groups

| TREATMENT GROUP | WBC | RBC | HGB | PLT | % RET |
|---|---|---|---|---|---|
| Saline (uninfected) ± | 5.00** | 10.83* | 17.04** | 1360.6** | 2.70 |
| | 0.92 | 0.06 | 0.16 | 27.44 | 0.17 |
| FLV-Saline ± | 40.99 | 9.28 | 13.83 | 514.57 | 10.48 |
| | 11.27 | 0.31 | 0.48 | 112.97 | 3.48 |
| FLV-Didox 450 ± | 3.13** | 4.23** | 6.83** | 97.60 | 1.68 |
| | 0.73 | 0.76 | 1.05 | 25.94 | 0.81 |

TABLE 2-continued

Blood Count and Percent Reticulocytes for Table 1 Groups

| TREATMENT GROUP | WBC | RBC | HGB | PLT | % RET |
|---|---|---|---|---|---|
| FLV-Amidox 225 ± | 8.18** | 8.79 | 13.52 | 438.98 | 2.60 |
| | 1.32 | 0.29 | 0.54 | 115.20 | 0.95 |
| Didox 450 ± | 2.84** | 8.87 | 14.60 | 333.74 | 1.65 |
| | 0.34 | 0.33 | 0.42 | 53.40 | 0.32 |
| Amidox 225 ± | 4.92** | 10.56 | 16.98* | 1158.2** | 1.74 |
| | 0.60 | 0.18 | 0.21 | 103.97 | 0.13 |

* and ** correspond to alpha levels of .05 and .01 respectively.
FLV = Friend leukemia virus infected group of mice.

As can be seen from the data presented in Tables 1–2, Didox reduced the splenomega-Ly associated with murine FLV infection to control levels, indicating an almost total suppression of the retrovirus. Liver weights in the Didox treated FLV infected group was not significantly increased over the uninfected group (saline control) weights whereas the FLV-infected mice showed an increase in liver weight. These results demonstrate the effectiveness of Didox in suppressing FLV because FLV infection in mice invariably gives an increase in spleen weight. Amidox gave a qualitatively similar effect. In the blood, the Didox-treated FLV-infected mice showed an essentially normal WBC (compared to the tremendous increase found in FLV infected mice). A second important indicator of the degree of viremia is the % of immature red blood precursors (reticulocytes) which increases with viremia. All of the treatment and control groups with Didox and Amidox gave essentially normal reticulocyte levels whereas the FLV-saline controls showed a marked increase in the percentage of reticulocytes. REBC and hemoglobin values were decreased compared to FLV-saline controls. Amidox gave similar, but not as pronounced, results. Both Didox and Amidox in the uninfected controls decreased platelet counts, as well as in the infected and the drug-alone control groups.

It is apparent from the above data that Didox, and to a lesser extent, Amidox, at the dose levels tested, are able to suppress growth of the retrovirus, FLV, in FLV-infected mice.

In a further exploration of the ability of Didox to suppress the growth of the retrovirus, FLV, Didox was administered as before to groups of IFLV-infected hybrid mice at dose levels varying from 28–450 mg/kg using the previous protocol. In addition, one group of mice treated at the 450 mg/kg level were sacrificed on day 28, rather than day 14 (although treatment was terminated on day 12 as before) as with the other groups of infected mice, in order to determine whether the positive effects seen at 14 days would persist. The results of that and the other experiments are given in TABLE 3 below.

TABLE 3

Relative Spleen and Liver Weights for Didox Treated Mice

| TREATMENT GROUP | SPLEEN WT. | LIVER WT. |
|---|---|---|
| | Mean ± S.E. | |
| Saline | 0.35 ± 0.01 | 4.75 ± 0.06 |
| FLV-Saline | 3.84 ± .180 | 5.77 ± 0.53 |
| FLV-450 Didox | 0.35 ± 0.03 | 5.71 ± 0.27 |
| FLV-450 Didox (28 day) | 1.50 ± 0.52 | 5.76 ± 0.27 |
| FLV-225 Didox | 1.89 ± 0.69 | 5.67 ± 0.19 |

TABLE 3-continued

Relative Spleen and Liver Weights for Didox Treated Mice

| TREATMENT GROUP | SPLEEN WT. | LIVER WT. |
|---|---|---|
| FLV-112.5 Didox | 4.39 ± 1.56 | 6.12 ± 0.51 |
| FLV-56.25 Didox | 5.40 ± 1.81 | 5.95 ± 0.57 |
| FLV-28 Didox | 4.94 ± 1.59 | 5.51 ± 0.36 |

All numbers in col. 1 refer to mg/kg of Didox for 12 days. Blood studies, as in Table 2, were carried out on the mouse groups in Table 3. Although not statistically significant, WBC and % reticulocytes were generally lower in the FLV-infected, Didox treated mice than in the FLV-infected untreated group. The higher dose levels (45 and 225 mg/kg) gave the most drastic reductions. A nearly three-fold increase in white blood cells (WBC) in the FLV-infected group was prevented by treatment with Didox with doses of 225 mg/kg or greater.

It is also apparent that, in FLV-infected mice, only the higher dose levels of Didox were effective to suppress the growth of the virus in vivo. In addition, the 450 mg/kg dose level of Didox demonstrated some long-lasting positive effects in FLV-infected mice long after the therapy had been terminated.

To test the ability of the polyhydroxybenzoic acid derivatives to suppress the growth of mammalian DNA viruses, anti-viral screening against the following human DNA viruses was performed in tissue culture employing N,3,4-trihydroxybenzamide (Didox), N,3,4-trihydroxybenzimldamide (Amidox) or N,3,4,5-tetrahydroxy-benzimidamide (Trimidox). The DNA viruses employed were Herpes Simplex Type 1 (HSV-1) and Herpes Simplex Type 2 (HSV-2). The primary screen utilized Human Foreskin Fibroblast cells with the following protocols: for HSV-1 or 2, a semi-automated CPE-inhibition assay was used employing HSV-1 E-377 strain and HSV-2 MS strain; for cytomegalo virus (CMV), semi-automated CPE inhibition assay using AD169 strain and for varicell-ovirus (VZV), a plaque reduction assay using ELLEN strain. Toxicity was determined by visual inspection of treated cells, generally stationary cells. A cell proliferation assay was carried out by determining the presence of rapidly growing cells and either an $EC_{50}$ (concentration required to inhibit viral cytopathogenicity by 50%) or an $IC_{50}$ (concentration ug/ml) required to inhibit cell proliferation 50%) was calculated. Also a Selective Index (S.I.) $IC_{50}/EC_{50}$ was determined.

Table 4 below gives the results of the Primary Screening Assay.

TABLE 4

| VIRUS | $EC_{50}$ | $IC_{50}$ | S.I. | ASSAY |
|---|---|---|---|---|
| DIDOX | | | | |
| HSV-1 | >20 | 48.9 | <2.5 | CPE |
| HSV-2 | >20 | 48.9 | <2.5 | CPE |
| HCMV | >20 | >100 | <5 | CPE |
| VZV | >20 | 49.9 | <2.5 | Pl.Red |
| TRIMIDOX | | | | |
| HSV-1 | >20 | 35.2 | <1.8 | CPE |
| HSV-2 | >20 | 35.2 | <1.8 | CPE |
| HCMV | >100 | >100 | <5 | CPE |
| VZV | >4 | 11.3 | <2.8 | Pl.Red |

The above HSV experiments were performed using a plaque reduction assay in 6-well plates and incorporation of the drug into an agarose overlay one hour after adsorption of the virus. The second set of experiments were performed using a 50% inhibition of cytopathic effect (CPE-50) endpoint in microliter plates and mixing dilutions of the drug with tissue culture media one hour after adsorption. Didox and Amidox were assayed for their inhibition of viral toxicity in tissue culture. Human Foreskin Fibroblasts (HFF) or Mouse Embryo Fibroblasts (MEF) were the cell lines employed. Viruses used were HSV-1 and HSV-2. A $CPE_{50}$, concentration of drug in mcg/ml which inhibited the cytopathic effect of the virus 50% was determined. Table 5 gives the results of these experiments.

TABLE 5

| VIRUS | CELL LINE | $CPE_{50}$ | DRUG |
|---|---|---|---|
| HSV-1 | HFF | 15.0 | Amidox |
| HSV-2 | | 18.0 | |
| HSV-1 | MEF | 6.0 | |
| HSV-2 | | 4.3 | |
| HSV-1 | HFF | >8.3 | Didox |
| HSV-2 | | >8.3 | |
| HSV-1 | MEF | >8.3 | |
| HSV-2 | | >8.3 | |

The compounds were more effective in the second set of experiments. Possibly the agarose overlay interfered with antiviral activity of the drugs in the first experiments.

Didox and Trimidox were also tested against Epstein Barr Virus (EBV) in Raji (a Burkitt's lymphoma cell line containing 60 EBV genomes/cell) cells. An immunofluorescence assay using monoclonal antibodies directed against EBV components were used to measure the quantity of virus. In this in vitro assay, Didox yielded an $EC_{50}$ of 0.69 and $IC_{50}$ of 2.8 while Amidox gave an $EC_{50}$ of 0.63 and $IC_{50}$ of 0.68.

Although two of the compounds represented by Formula I above, Didox and Amidox, were administered in saline to retrovirus infected mice by the intraperitoneal route, other parenteral routes (intravenous, intramuscular, intradermal or intrathecal) could also be used and the compounds formulated for such parenteral routes in accordance with the skill of the art, preferably in isotonic solution. The same considerations apply to oral medications containing Didox or Amidox, i.e., tablets, filled gelatin capsules, or liquid formulations.

Compounds according to Formula II above, being of roughly similar structure to those of Formula I, can be formulated similarly. The hydroxyureas and thiosemicarbazones useful in the therapeutic processes of this invention can be formulated in the same way as the hydroxyureas and thiosemicarbazones already marketed for various diseases.

As will be apparent also to those skilled in the art, the effective dose levels will vary according to the mode of administration. For example, oral dose levels would be higher, and intravenous or intramuscular levels lower in general than intraperitoneal dose levels. Drug carriers may also be employed and the viral suppressive agents of this invention can be combined in a combination dosage form with, or be administered at the same time as, other viral suppressive agents, immune stimulators and the like. Phenol-acetylated compounds, although called "pro-drugs" herein, can also be considered as a special type of drug carrier.

We claim:

1. A therapeutic procedure for treating mammalian diseases caused by retroviruses which comprises administering to a retrovirus infected mammal in need of treatment an effective amount of a ribonucleotide reductase inhibitor sufficient to at least partially suppress the growth or reproduction of said virus in said mammal.

2. A therapeutic process according to claim 1 in which the ribonucleotide reductase inhibitor is represented by the following formula

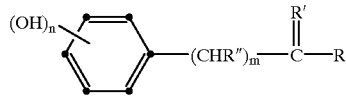

wherein n is 2–5, m is 0, R is $NH_2$, NHOH, $OC_{1-3}$ alkyl or O-phenyl, R' is O, NH, or NOH, R" is H or OH and pharmaceutically-acceptable acid-addition salts and acetylated phenol derivatives thereof.

3. A therapeutic process according to claim 2 in which the anti-viral drug is N,3,4-trihydroxybenzamide.

4. A therapeutic process according to claim 2 in which the anti-viral drug is N,3,4,5-tetrahydroxybenzimidamide.

5. A procedure according to claim 2 in which the retrovirus being treated is HIV-1 or HIV-2.

6. A procedure according to claim 1 in which the viral disease is caused by Friend leukemia virus and the infected mammal is a mouse.

7. A procedure according to claim 1 in which the viral disease being treated is caused by HIV-1 and the infected mammal is man.

8. A therapeutic process according to claim 1 in which the ribonucleotide reductase inhibitor has the following formula

wherein n is 2–5 and P is COOH, CN, $C_1$–$C_8$ alkyl, aryl-substituted $C_1$–$C_8$ alkyl, acylamino, $HOC_2H_4$—NH—$CH_2$—C(=O)—, Cl—$C_2H_4$—$NCH_3$—$CH_2$—C(=O)—, C(=S)$OC_2H_5$, C(=O)—NH—$C_{1-3}$ alkyl, C(=NH)—N(OH)—$C_{1-3}$ alkyl and substituted variants thereof.

9. A therapeutic process according to claim 1 in which the ribonucleotide reductase inhibitor employed is a compound of the formula $R^3Z$, wherein $R^3$ is H, $NH_2$, $NH_2$—NH, NHOH, NOH—$R^6$, $C_1$–$C_6$ alkyl, $OC_{1-6}$ alkyl, aryl-substituted $C_1$–$C_6$ alkyl, phenyl, naphthyl, pyridyl, pyrimidyl or thienyl and wherein Z is C(=O)NOH—$R^4$, C(=S)—NOH—$R^4$, C(=NH)—NOH—$R^4$, C(=NOH)—$C_1$–$C_3$ alkyl, C(=NOH)—$R^4$ and C(=NOH)—$R^5$, wherein $R^4$ is H, $C_1$–$C_6$ alkyl and substituted $C_1$–$C_6$ alkyl, wherein said substituents can be hydroxy, alkoxy, amino or halo, and wherein $R^5$ is $NH_2$ or NHOH, wherein $R^6$ is $C_{1-6}$ acyl, alkyl and substituted $C_{1-6}$ alkyl, wherein said substitutes can be hydroxyl, alkoxy, amino or halo.

10. A therapeutic process according to claim 9 in which the ribonucleotide redictase inhibitor employed is hydroxyurea.

11. A therapeutic process for treating mammalian diseases caused by DNA viruses which comprises administering to a DNA virus infected mammal in need of treatment an effective amount of a compound of the following formula sufficient to at least partially suppress the growth or reproduction of said virus in said mammal,

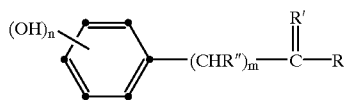

wherein n is 2–5, m is 0 or 1, R is $NH_2$, NHOH, $OC_{1-3}$ alkyl or O-phenyl, R' is O, NH, or NOH, R" is H or OH and pharmaceutically-acceptable acid-addition salts and acetylated phenol derivatives thereof.

12. A therapeutic process according to claim 11 in which the DNA virus is a herpes virus.

13. A therapeutic process according to claim 12 in which the herpes virus is Herpes simplex.

14. A therapeutic process according to claim 11 in which the DNA virus is a hepadnavirus.

15. A therapeutic process according to claim 14 in which the infecting virus is Hepatitis B.

16. A therapeutic process according to claim 11 in which the anti-viral drug is N,3,4-trihydroxybenzamide.

17. A therapeutic process according to claim 11 in which the anti-viral drug is N,3,4,5-tetrahydroxybenzimidamide.

18. A therapeutic process according to claim 1 in which the ribonucleotide reductase inhibitor is represented by the following formula

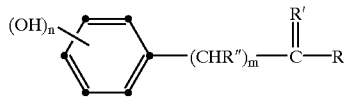

wherein n is 2–5, m is 1, R is $NH_2$, NHOH, $OC_{1-3}$ alkyl or O-phenyl, R' is O, NH or NOH, R" is H or OH and pharmaceutically-acceptable acid-addition salts and acetylated phenol derivatives thereof.

19. A therapeutic process according to claim 1 in which the ribonucleotide-reductase inhibitor is hydroxy urea, the retroviral disease is HIV-1 or HIV-2 and the diseased mammal is man.

* * * * *